United States Patent [19]

Anderson

[11] Patent Number: 5,329,012

[45] Date of Patent: Jul. 12, 1994

[54] BIS(ACYLOXMETHYL)IMIDAZOLE COMPOUNDS

[75] Inventor: Wayne K. Anderson, Williamsville, N.Y.

[73] Assignee: The Research Foundation of State University of New York, Albany, N.Y.

[21] Appl. No.: 114,695

[22] Filed: Oct. 29, 1987

[51] Int. Cl.$^5$ .................. C07D 233/90; C07D 233/64
[52] U.S. Cl. ........................... 548/318.5; 548/311.1; 548/319.5
[58] Field of Search ............ 548/337, 341, 342, 319.5; 514/398, 399, 400

[56] References Cited

U.S. PATENT DOCUMENTS

| | | | |
|---|---|---|---|
| 4,104,473 | 8/1978 | Sawa et al. ..................... | 548/342 |
| 4,122,277 | 10/1978 | Sawa et al. ..................... | 548/342 |
| 4,260,774 | 4/1981 | Atsumi et al. ................... | 548/337 |
| 4,658,035 | 4/1987 | Kempe et al. ................... | 548/342 |

OTHER PUBLICATIONS

El Borai et al, Chemical Abstracts, vol. 100, #85631n (1984).
Kempe et al, Chemical Abstracts, vol. 104, #224900x (1986).
Kempe et al, Chemical Abstracts, vol. 105, #42799j (1986).
Anderson, Wayne K., "Journal of Organic Chemistry", 1977, vol. 42, 559–561.

(List continued on next page.)

*Primary Examiner*—Floyd D. Higel
*Attorney, Agent, or Firm*—Bean, Kauffman & Spencer

[57] ABSTRACT

This invention relates to new bis(acyloxymethyl-)imidazole derivatives; to compositions comprising these derivatives; and to processes for their utility as fungicides, bactericides and as inhibitors of the growth of cancer, particularly solid tumor cancer, in warm blooded animals of the formula:

$$\begin{array}{c} R'' \\ | \\ R'-X-C \\ \diagdown \\ N \end{array} \begin{array}{c} N \\ \diagup \\ C-CH_2-OCM(=O) \\ \| \\ C-CH_2-OCM(=O) \end{array}$$

wherein M is $$N{<}^R_R$$

or R; each R, R' and R" are independently selected from hydrogen and Z substituted or unsubstituted alkyl, cycloalkyl, cycloalkenyl, alkenyl, aryl, and heterocyclic ring wherein said ring comprises at least one of oxygen, nitrogen, sulfur or silicon; provided that $$N{<}^R_R$$

may form a Z substituted or unsubstituted heterocyclic, and R' and R" attached to the imidazole ring, may form a Z substituted or unsubstituted heterocyclic ring; X is selected from at least one of oxygen, sulfur, nitrogen and alkyl; provided further that silicon is not directly attached to oxygen, sulfur or nitrogen and R' is not hydrogen when X is oxygen or sulfur; and Z is selected from halogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, sulfonylurea, sulfoxide, sulfone, substituted and unsubstituted amine or mixtures thereof.

45 Claims, No Drawings

OTHER PUBLICATIONS

Anderson, Wayne K., "Journal of Medicinal Chemistry", 1977, vol. 20, 812–818, 1691–1693.

Anderson, Wayne K., "Journal of Medicinal Chemistry", 1979, vol. 22, 977–980.

Anderson, Wayne K., "Journal of Medicinal Chemistry", 1980, vol. 23, 87–89.

Anderson, Wayne K., "Journal of Heterocyclic Chemistry", 1980, vol. 17, 513–517.

Anderson, Wayne K., "Arzneimittel-Forschung from Drug Research", 1980, vol. 30, 765–767.

Anderson, Wayne K., "Journal of Medicinal Chemistry", 1982, vol. 25, 84–86.

Anderson, Wayne K., "Cancer Treatment Reports", 1982, vol. 66, 91–97.

Anderson, Wayne K., "Cancer Research", 1982, vol. 42, 2168–2170.

Anderson, Wayne K., "Journal of Medicinal Chemistry", 1983, vol. 26, 1333–1338.

Anderson, Wayne K., "Journal of Medicinal Chemistry", 1984, vol. 27, 1321–1325, 1559–1565.

Anderson, Wayne K., "Journal of Organic Chemistry", 1985, vol. 50, 722–723.

Anderson, Wayne K., "Journal of Medicinal Chemistry", Nov. 1986, vol. 29, 2241–2249, 2392–2395.

Anderson, Wayne K., "Journal of Medicinal Chemistry", Nov. 1987, vol. 30, 2109–2115, 2144–2147.

BIS(ACYLOXYMETHYL)IMIDAZOLE COMPOUNDS

This invention was made in part with government support under Grant Number RO1-CA-22935 awarded by the Department of Health and Human Services and in part under contract with NCI, DHHS Contract Number CM-27570. The government has certain rights in this invention.

BACKGROUND OF THE INVENTION

There has been a continuing need for new chemical compounds which are effective in inhibiting the growth of bacteria and fungi organisms. There has also been a continuing need for chemical agents useful in the treatment of cancers in warm blooded animals, especially in human beings. Indeed, the concentrated effort of the National Cancer Institute over the last several years of their increased government funding has identified many new chemical compounds having efficiency in the inhibition of cancers in warm blooded animals, but which, for a multiple of reasons, have not been commercially used in human cancer clinical treatment.

An object of this invention is to provide new compounds and methods for inhibiting the growth of bacteria or fungi.

Another object of the invention is to provide new compounds and methods which are useful for inhibiting the growth of cancer, particularly solid tumor cancer.

DESCRIPTION OF THE INVENTION

This invention relates to new bis(acyloxymethyl-)imidazole derivatives; to their acid salts; to compositions comprising these derivatives; and to processes for their utility as fungicides, bactericides and as inhibitors of the growth of cancer, particularly solid tumor cancer, in warm blooded animals.

In accordance with this invention, new 4,5-bis-imidazole compounds are provided of the formula:

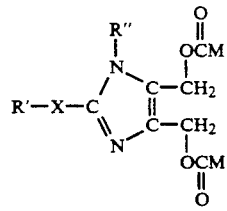

wherein M is

or R; each R, R', R" and are independently selected from hydrogen and Z substituted or unsubstituted alkyl, cycloalkyl, cycloalkenyl, alkenyl, aryl, and heterocyclic ring wherein said ring comprises at least one of oxygen, nitrogen, sulfur or silicon; provided that

may form a Z substituted or unsubstituted heterocyclic, and R' and R" attached to the imidazole ring, may form a Z substituted or unsubstituted heterocyclic ring; X is selected from at least one of oxygen, sulfur, nitrogen and alkyl; provided further that silicon is not directly attached to oxygen, sulfur or nitrogen and R' is not hydrogen when X is oxygen or sulfur; and Z is selected from halogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, sulfonylurea, sulfoxide, sulfone, substituted and unsubstituted amine, or mixtures thereof.

Further in accord with the invention, new pharmaceutical compositions are provided which contain the compounds of the invention in the form of their acid salts. Thus, new acid salt compounds are provided of the formula:

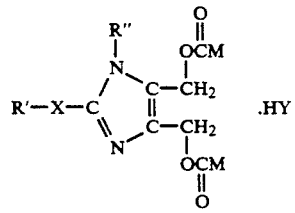

wherein Y is the anion of an acid and M, X, R' and R" are as previously described.

In addition, a method of the invention is provided where one or more of the afore-described compounds is administered to fungi or bacteria in an amount sufficient to inhibit the growth thereof.

In another method of the invention, one or more of the afore-described compounds is administered to a cancer, particularly solid tumor cancer, containing warm blooded animal in an amount sufficient to inhibit the growth of said cancer.

In a further mode of the invention, new intermediate 4,5-bis-imidazole compounds are provided of the formula:

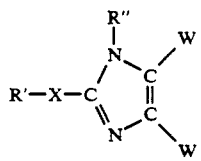

wherein each W is selected from

R"" is selected from hydrogen or substituted and unsubstituted alkyl, cycloalkyl, cycloalkenyl, alkenyl, and aryl; each R', and R" are independently selected from hydrogen and Z substituted or unsubstituted alkyl, cycloalkyl, cycloalkenyl, alkenyl, aryl, and heterocyclic ring wherein said ring comprises at least one of oxygen, nitrogen, sulfur or silicon; provided that R' and R" attached to the imidazole ring, may form a Z substituted or unsubstituted heterocyclic ring; X is selected from at least one of oxygen, sulfur, nitrogen and alkyl; provided further that silicon is not directly attached to oxygen, sulfur or nitrogen and R' is not hydrogen when X is oxygen or sulfur; and Z is selected from halogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, aulfonylurea, sulfoxide, sulfone, substituted and unsubstituted amine, or mixtures thereof.

Within the description of the compounds of the invention, particularly the designations R, R', R", R''', R'''', X and Z, by the term alkyl, alkenyl, cycloalkenyl, and cycloalkyl is meant alkyl, alkenyl, cycloalkenyl, and cycloalkyl hydrocarbon substituents having from 1 to about 20 carbon atoms and preferably from 1 to about 12 carbon atoms. Such substituents can be straight chained, branched, cyclic and include isomers thereof. Thus, the term alkyl includes methyl, ethyl, n-propyl, i-propyl, n-butyl, t-butyl, i-butyl, pentyl, hexyl, heptyl and the like up to about 20 carbon atoms. Similarly the term alkenyl includes unsaturated hydrocarbons having double bonds therein such as ethene, propene, butene, pentene and the like up to about 20 carbon atoms. By the terms cycloalkyl and cycloalkenyl is meant the alicyclic saturated and unsaturated hydrocarbons of up to about 20 carbon atoms such as cyclopropyl, methylcyclopropyl, cyclobutyl, ethylcyclobutyl, cyclopentyl, cyclohexyl and the like.

By the term heterocyclic ring is meant a cyclic compound containing carbon and noncarbon atoms as part of the cyclic structure. Such noncarbon atoms are meant to be limited to nitrogen, silicon, sulfur, and oxygen, with the heterocyclic containing up to about 20 carbon atoms with the attachment to the basic structure preferably, but not limited, to being through a carbon atom. Typical examples of appropriate heterocyclic substituents include piperidinyl, pyrrolyl, pyrrolizinyl, pyridyl, imidazolyl, furyl, morpholinyl, piperazyl, thiazolyl, thiomorpholinyl, tetrahydroquinolinyl, oxazolyl, azepinyl, indoxyl, indolizinyl and the like.

By the term substituted and unsubstituted amine is meant compounds of the formula: $-NR_2$, wherein each R is as previously described.

By the term aryl, is meant those cyclic aromatic and heteroaromatic structures which include benzene, naphthalene, pyridine, pyrimidine, quinoline, thiophene, indole, phenanthrene, anthracene, etc., up to a total of about 20 carbon atoms. The preferred aryl substituents are phenyl and napthyl.

When referring to haloalkyl is meant any alkyl group as previously described containing one or more halogen atoms, preferably chlorine, bromine and fluorine. By the term nitrile is meant cyano or alkyl cyanides of the general formula $RC{\equiv}N$ wherein R is substituted or unsubstituted as previously described.

By the term carboxylic acid is meant .an acid of the general structure:

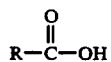

where R is substituted or unsubstituted as previously described, and particularly includes formic, acetic, propionic, butyric, valeric and the like carboxylic acids up to about 20 carbon atoms.

By the term carboxylic acid ester is meant an ester which can be derived through a carboxylic acid and generally includes compounds of the structure:

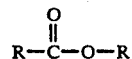

wherein each R is substituted or unsubstituted as previously described up to a total of about 20 carbon atoms. Generally, such esters can comprise straight hydrocarbon chains or branches and include the isomers thereof. Attachment can, of course, occur through the R group or directly to the carbonyl by loss of R group substituents, Typical examples include:

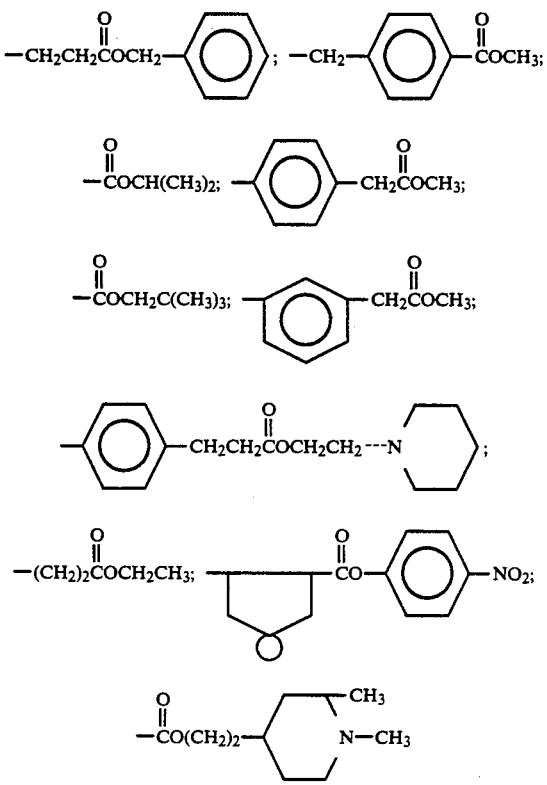

and the like.

By the term carboxylic acid amide, is meant a compound having the general formula $RCONH_2$, RCONHR OR $RCONR_2$, wherein R is substituted or unsubstituted as previously described up to about 20 carbon atoms. Typically, such amides can comprise straight hydrocarbon chains or branches and include the isomers thereof. Typical examples include

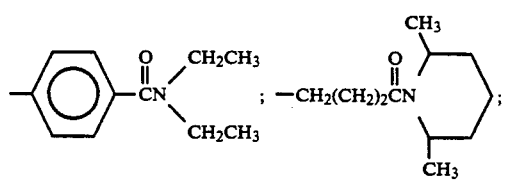

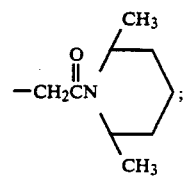

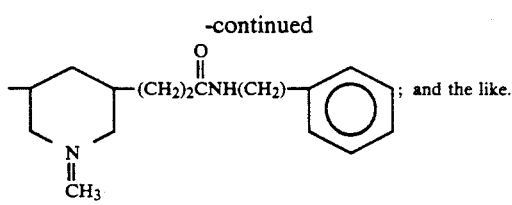; and the like.

By the term ether and thioether is meant compounds of the general formula R—O—R and R—S—R wherein R is substituted or unsubstituted as previously described up to about 20 carbon atoms. Generally, such ethers can comprise straight hydrocarbon chains or branched and include the isomers thereof. Thioether compounds are usually formed by the reaction of a thiol with an alkyl halide.

By the term sulfoxide, sulfone, sulfonylamide, and sulfonylurea is meant compounds of the formulae:

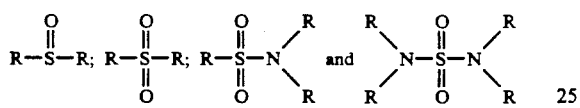

wherein R is substituted or unsubstituted as previously described up to about 20 carbon atoms. Such compounds can comprise straight hydrocarbon chains, branched or isomers thereof. Sulfoxides are usually made by oxidation of a corresponding sulfide with reagents such as nitric acid, chromium trioxide or hydrogen peroxide, and the corresponding sulfone is prepared by further oxidizing the sulfoxides with hydrogen peroxide or potassium permanganate.

By the term anion of an acid is meant the anion of any acid capable of forming an acid salt with the base structure. Generally, a strong mineral acid such as HCl, $H_2SO_4$ and the like is preferred for convenience in the manufacture of the acid salt, but generally, any acid, including acetic acid, the sulfonic acids and many of the carboxylic acids will readily form an acid salt with the base structure compounds of the invention.

Typically the preparation of the compounds of the invention can be attained through several routes, but we have generally obtained higher yields with routes in accordance with the following schematics:

(1)

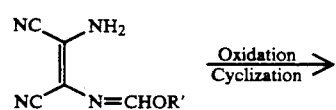

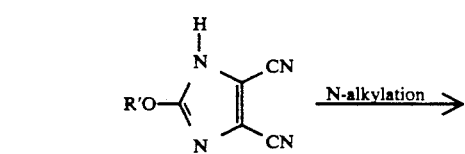

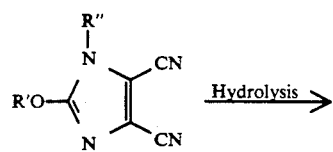

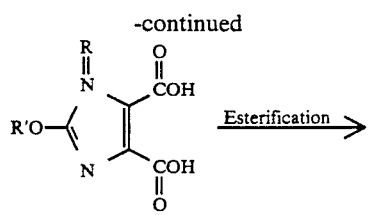

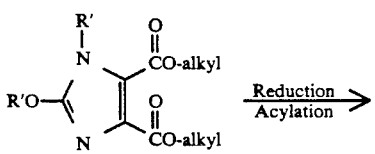

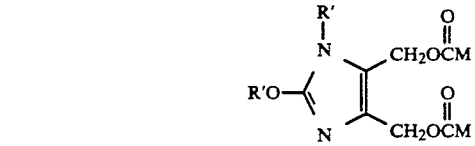

(2)

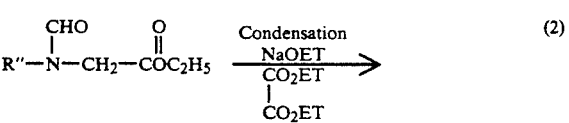

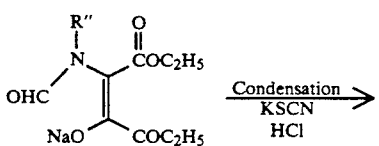

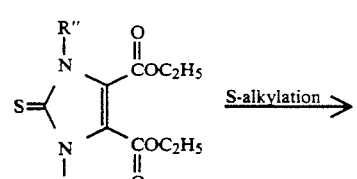

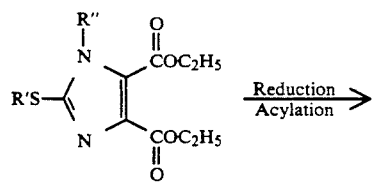

(3)

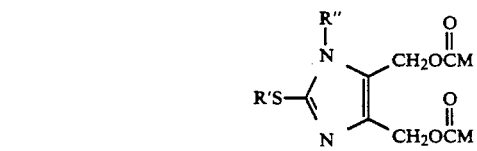

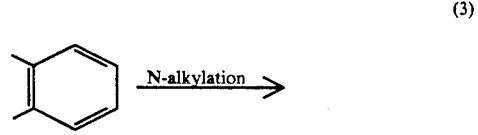

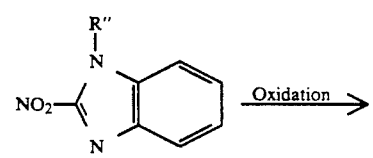

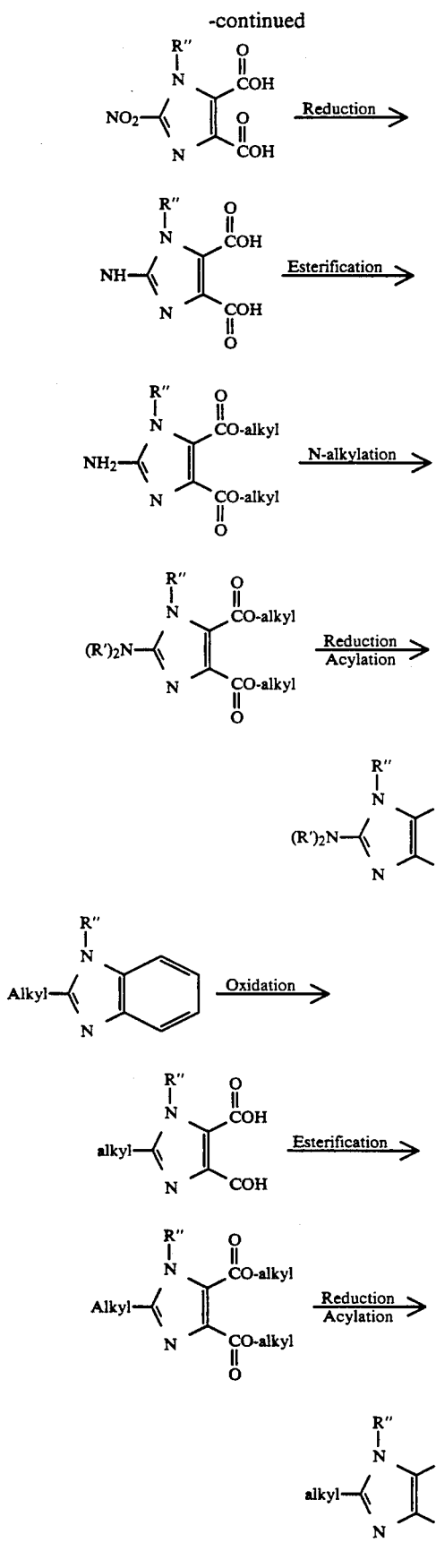

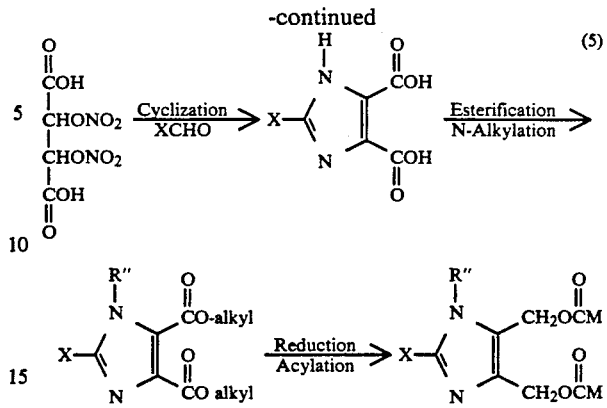

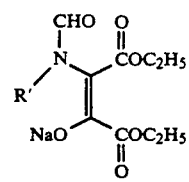

Wherein X is selected from Z substituted or unsubstituted alkyl, cycloalkyl, alkenyl, heterocyclic, and aryl.

Generally, in the route designated (1), the oxidation cyclization reaction results in adequate yields using 2,3-dichloro-5,6-dicyanobenzoquinone (DDQ) as the oxidant in acetonitrile at about reflux temperature. The N-alkylation steps of routes (1), (2) and (3) are generally run at ambient temperature using the appropriate R" or R' containing alkylating agent, in a polar, aprotic solvent such as N,N-dimethylformamide (DMF). The hydrolysis step of route (1) is conveniently accomplished by refluxing the reactant in an NaOH solution. The esterification step of routes (1) and (3)–(5) can generally be easily accomplished by leaving the reactant in solution with an appropriate diazoalkane at room temperature for several hours. The reduction and acylation steps of each of routes (1)–(5) is easily accomplished. For reduction, the reactant can be conveniently contacted with lithium aluminum hydride at ambient temperature. Acylation can be achieved with an appropriate isocyanate, acyl chloride or anhydride, with or without catalyst, at ambient temperature.

The condensation reaction in route (2) proceeds, at reflux, directly from the starting reactants to the sulfur substituted intermediate without the isolation of the compound:

The S-alkylation step is then run at ambient temperature using an appropriate R' halide with an alcohol solvent or an alkylating agent such as methyltrifluoromethylsulfonate in chloroform solvent.

The oxidation Steps of routes (3) and (4) have been found to be attainable at elevated temperatures using dichromate in sulfuric acid solution.

The formation of the acid salt of the bis (acyloxymethyl)imidazole compound can be easily accomplished by multiple means, generally utilizing any appropriate strong acid. For convenience the acid salt was typically made by treating the imidazole compound, in solution, with HCl and recovering the imidazole hydrochloride by crystallization.

The method in accordance with the present invention for inhibiting the growth of microorganisms and especially bacterial organisms comprises contacting the organism for a sufficient time with a sufficient concentration of the compounds, or compositions thereof, of the invention, suitable compounds being those previously generically and specifically described. In general the sufficient concentration of the compound is from about 0.01 to about 10 micrograms per milliliter of medium containing the organism. For very difficult microorganisms, e.g. fusobacteria, the concentration required may be substantially higher, e.g. as much as 50 micrograms per milliliter.

The medium on or within which the compounds of the invention can be used may be any solid or liquid. Examples of medium within or upon which the compounds may be used are organic tissue, surfaces, floors, walls, hardware, implements in general, paints, textiles, leather, synthetic resins, foods, medicines, and other like substances. The compounds may be used in or on the medium as antiseptics, disinfectants, antimicrobial medicines or preservatives. They also may be used as additives to soaps, deodorants, and sterilizing solutions to enhance or provide antimicrobial properties to such products. A compound of the invention may be used alone, in mixture With other compounds of the invention, in mixture with other inhibiting compounds, with diluents, extenders, and carriers or the like. It is to be understood that the above sufficient concentrations are those required to be in actual contact with the microorganism and substantially higher concentrations may be required in preparations where penetration through a substance is required in order to contact the microorganism with the compounds of the invention. The sufficient time is the time required to inhibit the growth of the microorganism and may depend upon the extent of inhibition required. Generally, the microorganism is inhibited by the compounds in from about 10 seconds to 30 minutes.

Microorganism as used herein includes any microorganism whose growth can be inhibited by the compositions of the invention. Such microorganisms include almost all bacteria and also include many fungi. It is also possible that some other protists and perhaps even some viruses are included.

As previously discussed, another method of the invention comprises the chemical inhibition of the growth of cancerous tumor cells. In accordance with this method, an organism containing tumor cells is administered an effective tumor inhibiting concentration of a pharmaceutical composition comprising at least one compound of the invention preferable in acid salt form.

The quantity of the compound sufficient for treatment of cancer tumors varies depending upon the size of the warm blooded animal involved, upon the type of solid tumor and upon the species of the animal involved. In general for most applications the effective tumor inhibiting concentration of the compound of the invention usually ranges between about 0.5 and 1500 milligrams per kilogram of body weight of the organism being treated. The preferred concentration is between about 1 and about 300 milligrams per kilogram of body weight of the organism being treated. In general, large animals require less of any pharmaceutical compound per kilogram of body weight than smaller animals.

The method of the invention has numerous advantages over prior treatment methods which will become clear from the specification as set forth below. The compounds of the invention have a broad range of activity against multiple tumors over a broad range of doses. This makes the drug much more suitable for widespread use against different types of tumors and lowers the risk of toxic dose.

As used herein the term leukemic cancer refers to all cancers or neoplasms of the hemopoietic and immune systems (blood and lymphatic system). The solid tumors as used herein are those epithelial neoplasms, such as skin and stomach cancer; connective tissue neoplasms, such as bone and smooth muscle cancer; neoplasms of the nervous system; neoplasms of multiple tissues, such as breast cancer and kidney cancer; and miscellaneous neoplasms such as placenta cancer and ovary cancer. Of particular interest herein are the solid cancer tumors of the colon, lung, and breast.

The solid tumors are believed more difficult to treat than leukemic cancers as they are slower growing and dense. It is believed that most treatment materials are effective at the time of cell division. The slower growth means fewer cell divisions cell. The dense mass of tumor does not allow as ready access of the treatment compound to the tumor as the more widely separated cells of the leukemic blood cancers. Therefore, the activity of the compounds of the invention against solid tumors is unusual and of interest for solid tumor treatment.

Any suitable dosage may be given in the method of the invention. The type of and the amount of dosage will vary widely depending on the species of the warm blooded animal, body weight, and tumor being treated. Generally, a dosage of between about 2 milligrams per kilogram of body weight and about 400 milligrams per kilogram of body weight is suitable. Generally, the dosage in man is lower than for small warm blooded mammals such as mice. A dosage unit may comprise a single compound of the invention or mixtures thereof with other compounds of the invention or other cancer inhibiting compounds. The dosage unit can also comprise diluents, extenders, carriers, and the like. The unit may be in solid or gel form such as pills, tablets, capsules, and the like or in liquid form suitable for oral, rectal, topical, or parenteral administration.

The method of treatment may be any suitable method which is effective in treatment of the particular tumor which is under treatment. Treatment may be oral, rectal, topical, parenteral, and the like. The method of applying an effective amount also varies depending on the tumor being treated. It is believed that parenteral treatment by intravenous, subcutaneous, or intramuscular application, formulated with an appropriate carrier, additional cancer inhibiting compound(s) or diluent to facilitate application, will be the preferred method of administering the compounds of the invention in warm blooded animals.

The following examples are meant to illustrate the invention and are not to be viewed as a limitation thereof. All temperatures are in degrees Centigrade unless otherwise denoted.

EXAMPLE 1

Preparation of 2-Methyl-4,5-imidazoledicarboxylic Acid

Method A. Tartaric acid dinitrate (0.67 mol) was neutralized to congo red test paper with concentrated ammonium hydroxide (500 mL). Additional concentrated ammonium hydroxide (50 mL) was added followed by an acetaldehyde solution [previously prepared by the careful addition of acetaldehyde (195 mL, 3.5 mol) to concentrated ammonium hydroxide (250 mL) with ice bath cooling]. The dry ice-acetone bath was replaced with ice-water and the reaction mixture was allowed to warm to room temperature over 16 hours. The precipitate was filtered, resuspended in water (400 mL) and stirred, the mixture was filtered and the solid was washed with water (3×75 mL), methanol (2×40 mL) and ether (2×40 mL), then dried under vacuum to give 70 g of the captioned product having a melting point of 274°–275° C.

Method B. 2-Methylbenzimidazole (5 g) was added to a mixture of conc. sulfuric acid (70 mL) and water (55 mL) at 90° C. This was followed by the careful addition of powdered potassium dichromate (37 g). After 15–20 min. the mixture was quenched with ice-cold water and cooled to 0° C. Crystallization was induced by scratching the sides of the vessel. The precipitated acid was filtered, washed with water, alcohol, and finally with ether to give 19 g of the captioned product.

EXAMPLE II

Preparation of Dimethyl 2-methyl-4,5-imidazoledicarboxylate 2-methyl-4,5-imidazoledicarboxylic acid (77-5 mmol) was suspended in absolute methanol (1.2 L, dried over magnesium turnings with a catalytic amount of carbon tetrachloride) and treated with hydrogen chloride gas (dried by bubbling through concentrated sulfuric acid) until the solution became saturated and all the diacid had dissolved. The mixture was stirred three weeks at room temperature. The solvent was removed, water (500 mL) was added, and the resultant suspension was stirred until all the residue had dissolved. This acidic solution was carefully treated with concentrated sodium hydroxide until a pH of 9 was obtained. The resultant precipitate was extracted with dichloromethane (3×150 mL). The extracts were combined, dried (magnesium sulfate), concentrated in vacuo, and the residue was crystalized from hot ethyl acetate to give the captioned diester in 26% yield having a melting point of 138°–140° C.

EXAMPLE III

Preparation of Dimethyl 1,2-dimethyl,4,5-imidazoledicarboxylate

A solution of diazomethane (1.5 g, 35.7 mmol) in ether (100 ml) was slowly added at 0° C. with stirring to a suspension of the ester prepared in Example II (4.2 g, 18.59 mmol) in ether (100 mL). After the addition was completed, the solution was stirred at room temperature overnight. Excess diazomethane was decomposed by the slow and careful addition of dilute acetic acid and the mixture was concentrated in vacuo. Water (50 mL) was added and the mixture was thoroughly extracted with dichloromethane. The organic phase was washed with water, saturated sodium bicarbonate and again with water. The solution was dried and the solvent was removed in vacuo to give the captioned compound (4.46 g; 100%).

EXAMPLE IV

Preparation of 1,2-dimethyl-4,5-bis(hydroxymethyl)imidazole

A. A solution of the diester product of Example III (23 mmol) in freshly distilled anhydrous dichloromethane (50 mL) was added slowly to a stirred suspension of lithium aluminum hydride (69 mmol) in anhydrous ether (140 mL) at 0°–5° C. The mixture was stirred at 0°–5° C. for 3 hours after the addition was completed, then for 1 hour at room temperature. The excess hydride was carefully decomposed by the slow, sequential addition of water (2.6 mL), 15% sodium hydroxide solution (2.6 mL), and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and concentrated to dryness in vacuo. The product was dried in vacuo and crystallized from tetrahydrofuran to give the captioned imidazole.

B. In a similar manner a solution of the diester of Example II (23 mmol) in anhydrous dichloromethane (50 mL) is slowly added to a stirred suspension of lithium aluminum hydride (69 mmol) in anhydrous ether (140 mL) at about 0°–5° C. The mixture is stirred at about 0°–5° C. for about 3 hours after the addition is completed, then for about 1 hour at about room temperature. The excess hydride is carefully decomposed by the slow, sequential addition of water, 15% sodium hydroxide solution, and water. The precipitate of inorganic salts is filtered and extracted continuously for about 24 hours with tetrahydrofuran heated under reflux in a Soxhlet apparatus. The tetrahydrofuran solution is combined with the filtrate and concentrated to dryness in vacuo. The product is dried and crystallized from tetrahydrofuran to give 2-methyl-4,5-bis(hydroxymethyl)imidazole.

EXAMPLE V

Preparation of 1,2-dimethyl-4,5-bis(N-methylcarbonyloxymethyl) imidazole

A mixture of the 1,2-dimethyl-4,5-bis(hydroxymethyl) imidazole (10 mmol), freshly distilled methylisocyanate (40 mmol) and anhydrous triethylamine (0.5 ml) in dichloromethane (75 ml) was stirred at room temperature for about 16 hours. The volatiles were removed in vacuo and the product recrystallized to give the captioned product.

In a similar manner 2-methyl-4,5-bis(hydroxymethyl) imidazole is reacted with methylisocyanate to give 2-methyl-4,5-bis(N-methylcarbonyloxymethyl) imidazole.

EXAMPLE VI

Preparation of 1-methyl-2-benzyl-4,5-bis(N-methyl carbonyloxymethyl)imidazole

Tartaric acid dinitrate (0.67 mol) was neutralized to congo red test paper with concentrated ammonium hydroxide (500 mL). Additional concentrated ammonium hydroxide (50 mL) was added followed by a phenylacetaldehyde solution [previously prepared by the careful addition of phenylacetaldehyde (3.5 mol) to concentrated ammonium hydroxide (250 mL) with ice bath cooling]. The dry ice-acetone bath was replaced with ice-water and the reaction mixture was allowed to warm to room temperature over 16 hours. The precipitate was filtered, resuspended in water (400 mL) and stirred, filtered and the solid was washed with water (3×75 mL), methanol (2×40 mL) and ether (2×40 mL), then dried under vacuum to give 2-benzyl-4,5-imidazoledicarboxylic acid.

The 2-benzyl-4,5-imidazoledicarboxylic acid (77.5 mmol) was suspended in absolute methanol (1.2 L, dried over magnesium turnings with a catalytic amount of carbon tetrachloride) and treated with hydrogen chloride gas (dried by bubbling through concentrated sulfuric acid) until the solution became saturated and all the diacid had dissolved. The mixture was stirred three weeks at room temperature. The solvent was removed, water (500 mL) was added, and the resultant suspension was stirred until all the residue had dissolved. This acidic solution was carefully treated with concentrated sodium hydroxide until a pH of 9 was obtained. The resultant precipitate was extracted with dichloromethane (3×150 mL). The extracts were combined, dried (magnesium sulfate), concentrated in vacuo, and the residue was crystalized from hot ethyl acetate to give dimethyl 2-benzyl-4,5-imidazoledicarboxylate.

A solution of diazomethane (1.5 g, 35.7 mmol) in ether (100 ml) was slowly added at 0° C. with stirring to a suspension of the above ester (18.59 mmol) in ether (100 mL). After the addition was completed, the solution was stirred at room temperature overnight. Excess diazomethane was decomposed by the slow and careful addition of dilute acetic acid and the mixture was concentrated in vacuo. Water (50 mL) was added and the mixture was thoroughly extracted with dichloromethane. The organic phase was washed with water, saturated sodium bicarbonate and again with water. The solution was dried and the solvent was removed in vacuo to give dimethyl 1-methyl-2-benzyl-4,5-imidazole dicarboxylate.

A solution of the above-prepared diester (23 mmol) in freshly distilled anhydrous dichloromethane (50 mL) was added slowly to a stirred suspension of lithium aluminum hydride (69 mmol) in anhydrous ether (140 mL) at 0°-5° C. The mixture was stirred at 0°-5° C. for 3 hours after the addition was completed, then for 1 hour at room temperature. The excess hydride was carefully decomposed by the slow, sequential addition of water (2.6 mL), 15% sodium hydroxide solution (2.6 mL), and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and concentrated to dryness in vacuo. The product was dried in vacuo and crystallized from tetrahydrofuran to give 1-methyl-2-benzyl-4,5-bis (hydroxymethyl) imidazole.

A mixture of the above-prepared diol (10 mmol) and freshly distilled methylisocyanate (30 mmol) in anhydrous dichloromethane (100 mL) was treated with 2-3 drops of dibutyltin diacetate. The mixture was stirred at room temperature for 3 hours then the volatiles were removed in vacuo and the product was crystallized from dichloromethane-hexanes and dried in vacuo to give 1-methyl-2-benzyl-4,5-bis (N-methylcarbonyloxymethyl)imidazole.

EXAMPLE VII

Preparation of 1-methyl-2-methoxy-4,5-bis [N-( 2-propyl)carboxymethyl]imidazole

Trimethyl orthoformate (31-8 g; 0.3 mol) was added dropwise to a slowly distilling solution of diaminomaleonitrile (32.4 g; 0.3 tool) in 1,4-dioxane (250 mL). The methanol that formed during the reaction was removed by distillation. The reaction mixture was concentrated in vacuo and cooled to room temperature. The precipitate was collected and crystallized from THF-pentane to yield 33.6 g (62%) of 2-amino-3-(methoxymethylenamino) maleonitrile having a melting point of 138°-139° C.

A solution of the above 2-amino-3-(methoxymethylenamino) maleonitrile (20 g; 0. 11 mol) and 2,3-dichloro-5,6-dicyanobenzoquinone (25.5 g; 0.11 mol) in acetonitrile (750 mL) was heated at reflux for 4 days. Silica gel (100 g) was added and the acetonitrile was removed in vacuo. The silica gel was extracted with dichloromethane. The dichloromethane solution was concentrated to dryness in vacuo, the yellow residue was suspended in dichloromethane (150 mL) and the mixture was stirred. The mixture was filtered and the filtrate was concentrated in vacuo to yield a light yellow solid that was crystallized from water to give 2-methoxy-4,5-imidazoledicarbonitrile (mp 137°-138° C.).

Sodium hydride g; 60% in an oil dispersion) was added in small portions to a stirred solution of the above-identified 2-methoxy-4,5-imidazoledicarbonitrile (3.25 g; 0.022 mol) in dimethylformamide (25 mL). Hydrogen gas was evolved. The mixture was cooled, iodomethane (3.2 g) was slowly added and the mixture was stirred overnight. The mixture was poured into ice-water and extracted with chloroform. The combined chloroform extract was washed with water, dried (magnesium sulfate) and concentrated to dryness in vacuo. The residue was chromatographed (silica gel eluted with dichloromethanehexanes) and the product was crystallized from dichloromethane-hexanes to give 1.6 g (45%) of 1-methyl-2-methoxy-4,5-imidazoledicarbonitrile (top 65°-66 ° C.).

A mixture of the above 1-methyl-2-methoxyimidazole-4,5-dicarbonitrile (1 g; 0.0062 mol) and 10% sodium hydroxide solution (30 mL) was heated at reflux for 4 hours (ammonia was evolved). The mixture was cooled, water (130 mL) was added and the mixture was neutralized with conc. hydrochloric acid. The precipitate was collected, dried (0.81 g; 65%) and crystallized from 90% ethanol to give 1-methyl-2-methoxy-4,5-imidazoledicarboxyclic acid as colorless crystals: mp 192°-4° C.

The 1-methyl-2-methoxy-4,5-imidazoledicarboxylic acid (8.0 g; 0.04 mol) was slowly added in small portions to a solution of diazomethane (3 g) in ether (nitrogen was evolved). The mixture was allowed to stand overnight at room temperature, the excess diazomethane was decomposed by the addition of dilute acetic acid, and the mixture was concentrated to dryness in vacuo. Water (100 mL) was added to the residue and the suspension was neutralized by the addition of sodium bicarbonate. The mixture was extracted with dichloromethane, the organic phase was dried (sodium sulfate) and concentrated to dryness in vacuo. The oily residue slowly crystallized and the solid was recrystallized from dichloromethane-hexanes to give 7.60 g (83%) of dimethyl 1-methyl-2-methoxy-4,5-imidazoledicarboxylate (mp 62°-63° C.).

A solution of the above-identified diester (23 mmol) in freshly distilled anhydrous dichloromethane (50 mL) was added slowly to a stirred suspension of lithium aluminum hydride (69 mmol) in anhydrous ether (140 mL) at 0°-5° C. The mixture was stirred at 0°-5° C. for 3 hours after the addition was completed, then for 1 hour at room temperature. The excess hydride was carefully decomposed by the slow, sequential addition of water (2.6 mL), 15% sodium hydroxide solution (2.6 mL), and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and concentrated to dryness in vacuo. The product was dried in vacuo and crystallized from tetrahydrofuran to give 1-methyl-2-methoxy-4,5-bis(hydroxymethyl)imidazole having a melting point of 110°–119° C.

A mixture of the above-identified diol (10 retool) and freshly distilled isopropylisocyanate (40 mmol) in anhydrous dichloromethane (100 mL) was treated with 2–3 drops of dibutyltin diacetate. The mixture was stirred at room temperature for 8 hours then the volatiles were removed in vacuo and the product was crystallized from dichloromethane-hexanes and dried in vacuo to give: (88%; mp 112°–113° C.) 1-methyl-2-methoxy-4,5-bis[N-(2-propyl)carbonyloxymethyl]imidazole (mp 112°–113° C.).

EXAMPLE VIII

Preparation of 1-phenyl-2-(methylthio)-4,5-bis(N-methyl carbonyloxymethyl)imidazole A mechanically stirred mixture of aniline (71 g; 0.76 mol), ethylbromoacetate (127.5 g; 0.76 mol), and anhydrous sodium acetate (62.6 g; 0.76 mol) in absolute ethanol (10 mL) was heated at reflux for 6 hours. The mixture was cooled, water was added to precipitate the product, and the solid was filtered and dried. The crude product was crystallized from ethanol-water to give N-phenylglycine ethyl ester (107 g; 79%) having amp 48°–49° C.

N-Phenylglycine ethyl ester (100 g; 0–56 mol) was added in small portions to acetic formic anhydride (100 g; 1.14 mol) with vigorous stirring. The mixture was allowed to stir overnight, then it was poured into water, and extracted with ether. The ether solution was washed with sodium bicarbonate solution and then with water. The ether was evaporated in vacuo to give an oil which was distilled to give N-phenyl-N-formylglycine ethyl ester (81 g; 70%) having a bp 115°–117° C.

Absolute ethanol (50 mL) was slowly added to a mechanically stirred suspension of finely cut sodium metal (19.3 g; 0.84 mol) in anhydrous ether (500 mL). When most of the metal had dissolved, diethyl oxalate (114 mL; 0.84 mol) was slowly added followed by the slow addition of the N-phenyl-N-formylglycine ethyl ester (130 g; 0.67 mol). The mixture was stirred at room temperature overnight and then ice-water (700 mL) was added. The resulting emulsion was broken by sequential addition of a saturated sodium chloride solution (150 mL) and water (200 mL). The aqueous layer was removed, potassium thiocyanate (114 g; 1.18 mol) was added, then concentrated hydrochloric acid (160 mL), followed by absolute ethanol (900 mL). The resultant mixture was warmed at 60°–65° C. for 1 hour, then at 50° C. for 6 hours and finally allowed to stir at room temperature overnight. The light yellow precipitate was filtered, washed with ethanol and dried to give 103 g (48%) of diethyl 2-mercapto-1-phenyl-4,5-imidazoledicarboxylate (mp 145°–146° C.).

Sodium methoxide (1.8 g; 0.033 mol) was slowly added to a suspension of diethyl 2-mercapto-1-phenyl-4,5-imidazoledicarboxylate (10 g; 0.031 mol) in absolute methanol (100 mL) then iodomethane (5 g; 0.035 mol) was added. The mixture was allowed to stir overnight, additional iodomethane (5 g; 0.035 mol) was added and the mixture was stirred for 1 hour. The methanol was removed in vacuo and ice-cold water was added to the residue. The mixture was filtered, the collected solid was washed with water and dried to give 7.6 g (80%) of pure dimethyl 2-(methylthio)-1-phenyl-4,5-imidazoledicarboxylate (mp 121°–122° C).

A solution of the above diester (23 mmol) in freshly distilled anhydrous dichloromethane (50 mL) was added slowly to a stirred suspension of lithium aluminum hydride (69 mmol) in anhydrous ether (140 mL) at 0°–5° C. The mixture was stirred at 0°–5° C. for 3 hours after the addition was completed, then for 1 hour at room temperature. The excess hydride was carefully decomposed by the slow, sequential addition of water (2.6 mL), 15% sodium hydroxide solution (2.6 mL), and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and concentrated to dryness in vacuo. The product was dried in vacuo and crystallized from tetrahydrofuran to give 1-phenyl-2-(methylthio)-4,5-bis (hydroxymethyl)imidazole.

A mixture of the above diol (10 mmol), freshly distilled methylisocyanate (30–40 mmol) and anhydrous triethylamine (0.5 mL) in dichloromethane (75 mL) was stirred at reflux for 6 days. The volatiles were removed in vacuo and the product was crystallized from ethyl acetate and dried in vacuo to give the captioned product (82%; mp 137°–138° C.).

EXAMPLE IX

Preparation of 2-(methylthio)-4,5-bis[N-(2-propyl) carbonyloxymethyl]imidazole

A hot solution of sodium formate (150 g) in formic acid (200 mL) was added to a hot solution of glycine ethyl ester hydrochloride (228.7 g; 1.64 mol) in hot formic acid (250 mL). This was allowed to stir at room temperature for 1 hour (sodium chloride separated). Small portions of acetic anhydride (450 g) were added to the well-stirred suspension as an exothermic reaction ensued. The suspension was stirred overnight, the solid was filtered and the filtrate was distilled in vacuo to remove excess reagents. The residue was filtered and then distilled to give N-formylglycine ethyl ester (182 g; 85%) as a colorless liquid having a bp 105°–100° C. under vacuum.

Absolute ethanol (58 g; 1.25 mol) was added to a suspension of clean sodium (29 g; 1.25 g atom cut into small pieces) in anhydrous ether (700 mL). Diethyl oxalate (182 g; 1.25 mol) was added slowly to this mixture so that the exothermic reaction did not become too vigorous. The N-formyl-glycine ethyl ester (131 g; 1.0 mol) was added dropwise with stirring to the resulting solution and a red-brown precipitate formed. The mixture was allowed to stand overnight then water (1 L) was added to dissolve the precipitate and the ether layer was separated. Potassium thiocyanate (170 g; 1.75 mol) and concentrated hydrochloric acid (240 mL) were added to the aqueous solution. The yellow aqueous solution was slowly heated to 40°–60° C. for 6 hours and cooled. The yellow granular precipitate was filtered. The filtrate was concentrated to give an additional amount of the same product. The total product yield of 109.0 g (45%) of diethyl 2-mercapto-4,5-imidazoledicarboxylate was obtained.

Iodomethane (15.62 g; 0.11 mol) was added to a solution of 24.4 g (0.10 mol) of diethyl 2-mercapto-4,5-imidazoledicarboxylate and sodium methoxide (6.0;

0.11 mol) in absolute methanol (500 mL) at room temperature. Additional iodomethane (5g) was added after 1 hour and the yellow solution was allowed to stir at room temperature for 3 hours. The methanol was then removed in vacuo, the residue was treated with cold water and the light yellow solid was filtered and dried to give diethyl 2-methylthio-4,5-imidazoledicarboxylate (22.3 g; 86%).

The diethyl 2-(methylthio)-4,5-imidazoledicarboxylate (10 g; 0.039 mol) was slowly added in small portions to a solution of diazomethane in ether (containing approximately 3 g of diazomethane). Nitrogen was evolved immediately and the solution was allowed to stand at room temperature overnight. Excess diazomethane was then decomposed by the addition of dilute acetic acid and the reaction mixture was worked up in the usual way. Diethyl 1-methyl-2-(methylthio)-4,5-imidazoledicarboxylate (10.2 g; 97%) was obtained as a thick yellow oil.

A solution of the above diethyl 2-(methylthio)-4,5-imidazoledicarboxylate (23 mmol) in freshly distilled anhydrous dichloromethane (50 mL) is added slowly to a stirred suspension of lithium aluminum hydride (69 mmol) in anhydrous ether (140 mL) at 0°–5° C. The mixture is stirred at about 0°–5° C. for about 3 hours after the addition is completed, then for about 1 hour at room temperature. The excess hydride is carefully decomposed by the slow, sequential addition of water (2.6 mL), 15% sodium hydroxide solution (2.6 mL), and water (7.8 mL). The precipitate of inorganic salts is filtered and extracted continuously for about 24 hours with tetrahydrofuran heated under reflux in a Soxhlet apparatus. The tetrahydrofuran solution is combined with the filtrate from the reaction mixture and concentrated to dryness in vacuo. The product is dried in vacuo and crystallized from tetrahydrofuran to give 2-(methylthio)-4,5-bis(hydroxymethyl) imidazole.

In a similar manner, the diethyl 1-methyl-2-(methylthio)-4,5-imidazoledicarboxylate diester was treated to give the 1-methyl-2-(methylthio)-4,5-bis(hydroxymethyl)imidazole.

A mixture of the above 2-(methylthio)-4,5-bis(hydroxymethyl) imidazole diol (10 mmol) and freshly distilled isopropylisocyanate (30–40 retool) in anhydrous dichloromethane (100 mL) was treated with 2–3 drops of dibutyltin diacetate. The mixture was stirred at room temperature for 3 hours then the volatiles were removed in vacuo and the product was crystallized from dichloromethane-hexanes and dried in vacuo to give the captioned product.

In a similar manner, the 1-methyl-2-(methylthio)-4,5-bis(hydroxymethyl)imidazole was treated to obtain a 94% yield of 1-methyl-2-(methylthio)-4,5-bis[N-(2-propyl)carbonyloxymethyl]imidazole (mp 105°–107° C.).

EXAMPLE X

Preparation of 1-methyl-2-dimethylamino-4,5-bis [N-(2-propyl)carbonyloxymethyl]imidazole To a solution of 0.185 mol of diaminomaleonitrile in 150 ml of dimethyl formamide at about 10° C. was added dropwise, over about 30 minutes, 0.155 mol of phosphorus oxychloride. After about 3 hours the resulting precipitate was quenched in water to produce 2-amino-3-(N,N-dimethylamino methyleneamino) maleonitrile (mp.148°–150° C.).

A solution containing 0.104 mol of the above maleonitrile in 600 ml of acetonitrile and 23.54 grams of DDQ was refluxed and the solvent removed in vacuo to produce 2-dimethylamino-4,5-imidazoledinitrile.

N-methylation of the dinitrile is accomplished in accord with Example VI, with excess diazomethane followed by hydrolysis with 10% aqueous sodium hydroxide at about reflux in accord with the process of Example VII to obtain 2-dimethylamino-3,4-imidazoledicarboxylic acid. The remaining processing steps are in accord with Example VII wherein the diacil is converted to the diester with diazomethane; the diester is reduced to the diol with lithium aluminum hydroxide; and the diol is converted to 1-methyl-2-dimethylamino-4,5-bis[N-(2-propyl)carbonyloxymethyl]imidazole.

EXAMPLE XI

Preparation of Diethyl 2-(methylthio)imidazole-4,5-dicarboxylate

A hot solution of sodium formate (150 g) in formic acid (200 mL) was added to a hot solution of glycine ethyl ester hydrochloride (228.7 g; 1.64 mol) in hot formic acid (250 mL). This was allowed to stir at room temperature for 1 hour. Small portions of acetic anhydride (450 g) were added to the well-stirred suspension as an exothermic reaction ensued. The suspension was stirred overnight, the solid was filtered and the filtrate was distilled in vacuo to remove excess reagents. The residue was filtered and then distilled to give N-formylglycine ethyl ester (182 g; 85%) having a boiling point of 105°–110° C. under vacuum.

Absolute ethanol (58 g; 1.25 mol) was added to a suspension of clean sodium (29 g; 1.25 g atom cut into small pieces) in anhydrous ether (700 mL). Diethyl oxalate (182 g; 1.25 mol) was added slowly to this mixture so that the exothermic reaction did not become too vigorous. The N-formyl-glycine ethyl ester (131 g; 1.0 mol) above formed was added dropwise with stirring to the resulting solution and a red-brown precipitate formed. The mixture was allowed to stand overnight then water (1 L) was added to dissolve the precipitate and the ether layer was separated. Potassium thiocyanate (170 g; 1.75 mol) and concentrated hydrochloric acid (240 mL) were added to the aqueous solution. The yellow aqueous solution was slowly heated to 40°–60° C. for 6 hours and cooled. The yellow granular precipitate was identified as diethyl 2-mercapto-4,5-imidazole-dicarboxylate (109.0 g; 45%).

Iodomethane (15.62 g; 0.11 mol) was added to a solution of 24.4 g (0.10 mol) of the above-produced diethyl 2-mercapto-4,5-imidazole-dicarboxylate (24.4 g; 0.10 mol) and sodium methoxide (6.0; 0.11 mol) in absolute methanol (500 mL) at room temperature. Additional iodomethane (5 g) was added after 1 hour and the yellow solution was allowed to stir at room temperature for 3 hours. The methanol was then removed in vacuo, the residue was treated with cold water and the light yellow solid was filtered and dried to give diethyl 2-(methylthio)imidazole-4,5-dicarboxylate (22.3 g; 86%).

EXAMPLE XII

Preparation of Diethyl 2-(methylthio)imidazole-4,5-dicarboxylate

Iodomethane (15.62 g; 0.11 mol) was added to a solution of 24.4 g (0.10 mol) of diethyl 2-mercaptoimidazole-4,5-dicarboxylate produced in accord with Example XI and sodium methoxide (6.0; 0.11 mol) in absolute methanol (500 mL) at room temperature. Additional iodomethane (5g) was added after 1 hour and the yellow solution was allowed to stir at room temperature for 3 hours. The methanol was then removed in vacuo, the residue was treated with cold water and the light yellow solid was filtered and dried to give diethyl 2-(methylthio)imidazole-4,5-dicarboxylate (22.3 g; 86%).

EXAMPLE XIII

Preparation of 1-methyl-2-methylthio)-4,5-bis (N-methylcarbonyloxymethyl) imidazole Diethyl 2-(methylthio)imidazole-4,5-dicarboxylate (10 g; 0.039 tool) was slowly added in small portions to a solution of diazomethane in ether (containing approximately 3 g of diazomethane). Nitrogen was evolved immediately and the solution was allowed to stand at room temperature overnight. Excess diazomethane was then decomposed by the addition of dilute acetic acid and the reaction mixture was worked up in the usual way. Diethyl 1-methyl-2-(methylthio)imidazole-4,5-dicarboxylate (10.2 g; 97%) was obtained as a thick yellow oil.

A solution of the above diester (23 mmol) in freshly distilled anhydrous dichloromethane (50 mL) was added slowly to a stirred suspension of lithium aluminum hydride (69 mmol) in anhydrous ether (140 mL) at 0°–5° C. The mixture was stirred at 0°–5° C. for 3 hours after the addition was completed, then for 1 hour at room temperature. The excess hydride was carefully decomposed by the slow, sequential addition of water (2.6 mL), 15% sodium hydroxide solution (2.6 mL), and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and concentrated to dryness in vacuo. The product was dried in vacuo and crystallized from tetrahydrofuran to give 1-methyl-2-(methylthio)-4,5-bis(hydroxymethyl)imidazole (79%; mp 119°–120° C.).

A mixture of the above-identified diol (10 mmol) and freshly distilled isocyanate (30 mmol) in anhydrous dichloromethane (100 mL) was treated with 3 drops of dibutyltin diacetate. The mixture was stirred at room temperature for 3 hours then the volatiles were removed in vacuo and the product was crystallized from dichloromethane-hexanes and dried in vacuo to give the captioned product (77%; mp 124°–1 25° C.).

EXAMPLE XIV

Preparation of Diethyl 2-(n-propylthio)imidazole-4,5-dicarboxylate

Sodium (0.253 g, 11 mmol) was dissolved in anhydrous methanol (150 mL) with ice-bath cooling. The ice-bath was removed after all the sodium had reacted and diethyl 2-mercapto-4,5-imidazoledicarboxylate prepared in accord with the second paragraph of Example XI (2.44 g, 10 mmol) was added. The appropriate n-propyl iodide (11 mmol) was added and the reaction mixture was stirred at ambient temperature under a nitrogen atmosphere for 1 hour. A second aliquot of n-propyliodide (3.52 mmol) was added and the solution was stirred for an additional 3 hours. The reaction mixture was concentrated to dryness in vacuo. The residue was partitioned between dichloromethane-water (5:1). The organic layer was separated, dried (sodium sulfate), filtered and concentrated to dryness in vacuo to give the captioned product as an oil.

EXAMPLE XV

Preparation of Diethyl 2-(n-hexylthio)imidazole-4,5-diacarboxylate

Sodium (0.253 g, 11 mmol) was dissolved in anhydrous methanol (150 mL) with ice-bath cooling. The ice-bath was removed after all the sodium had reacted and diethyl 2-mercapto- 4,5-imidazoledicarboxylate prepared in accordance with Example IX (2.44 g, 10 mmol) was added. The appropriate n-hexyl iodide (11 mmol) was added and the reaction mixture was stirred at ambient temperature under a nitrogen atmosphere for 1 hour. A second aliquot of n-hexyl iodide (3.52 mmol) was added and the solution was stirred for an additional 3 hours. The reaction mixture was concentrated to dryness in vacuo. The residue was partitioned between dichloromethane-water (5:1). The organic layer was separated, dried (sodium sulfate), filtered and concentrated to dryness in vacuo to give the captioned product as an oil.

EXAMPLE XVI

Preparation of 1-n-propyl-2-(methylthio)-4,5-bis (N-methylcarbonyloxymethyl)imidazole A. Sodium hydride was carefully added to a cooled (0°–5° C.) solution of the product of Example XI (10 mmol) and the appropriate n-propyl iodide (19.8 mmol) in anhydrous dimethylformamide (30 mL). The reaction mixture was allowed to stir under a nitrogen atmosphere at ambient temperature for 4 hours. The reaction mixture was cooled (0°–5° C.) and carefully quenched with ethanol (10 mL). The mixture was concentrated in vacuo at 40° C. (overnight) to give an oily residue that was treated with water (50 mL) and dichloromethane (100 mL). The aqueous layer was separated and extracted with dichloromethane. The combined dichloromethane solution was dried (sodium sulfate), filtered through a glass wool plug and concentrated to dryness in vacuo. The residue was treated with chloroform (500 mL) and filtered. The filtrate was concentrated to dryness in vacuo [silica gel/chloroform-methanol (19:1)] to give a residue, identified as diethyl 1-n-propyl-2-(methylthio)imidazole-4,5-dicarboxylate.

In a similar manner using the same reactants and conditions as the above, with the exception that n-hexyliodide was substituted for n-propyliodide, the final product was identified as diethyl 1-n-hexyl-2-(methylthio)imidazole-4,5-dicarboxylate.

B. A solution of the above-identified diethyl 1-n-propyl-2-(methylthio)imidazole-4,5-dicarboxylate (23 mmol) in anhydrous dichloromethane (50 mL) was slowly (1 hour) added to a stirred suspension of lithium aluminum hydride (69 mmol) in anhydrous ether (140 mL) at 0.5° C. under nitrogen. The mixture was stirred at 0°–5° C. for 3 hours after the addition was completed, then at ambient temperature for 1 hour. The excess hydride was carefully decomposed by the slow sequential addition of water (2.6 mL), 15% sodium hydroxide solution (2.6 mL) and water (7.8 mL). The precipitate of inorganic salts was filtered and extracted continuously for 24 hours with tetrahydrofuran heated under reflux in a Soxhlet apparatus. The tetrahydrofuran solution was combined with the filtrate from the reaction mixture and reduced to dryness in vacuo. The solid residue was crystallized from acetone and identified as 1-n-propyl-2-(methylthio)-4,5-bis(hydroxymethyl)imidazole (48% yield).

Similarly, 23 mmol of Diethyl 1-n-hexyl-2-(methylthio)imidazole-4,5-dicarboxylate was treated by the same process to yield 1-n-hexyl-2-(methylthio)-4,5-bis(hydroxymethyl)imidazole (62% yield).

C. A mixture of the above-identified 1-n-propyl-2-(methylthio)4,5-bis(hydroxymethyl)imidazole (10 mmol) and methylisocyanate (35 mmol) in anhydrous dichloromethane (100 mL) was treated with dibutyltin diacetate (2 drops). The mixture was stirred under nitrogen at ambient temperature for 5-10 hours and the volatiles were removed in vacuo. The residue was crystallized from acetone to provide the captioned product in 56% yield (top 129.5°-131° C.).

Using the same procedure, reactants and conditions with the exception that the diol was 1-n-hexyl-2(methylthio)4,5-bis(hydroxymethyl)imidazole, the resulting product is 1-n-hexyl-2-methylthio-4,5-bis(N-methylcarbonyloxylmethyl)imidazole (78% yield: mp 122°-123° C.).

EXAMPLE XVII

Formation of Hydrochloride Salts

Method A

A solution of the 1-n-propyl-2-methylthio-4,5-bis(N-methyl carbonyloxymethyl)imidazole prepared in Example XVI (1.72 g; 5.21 mmol) in anhydrous dichloromethane (50 mL) was stirred at 0°-5° C. while anhydrous hydrogen chloride gas was bubbled into the solution for 5 minutes through a gas dispersion tube. The solution was immediately reduced to dryness in vacuo at room temperature to give a white solid foam. The residue was dried in vacuo for 10 minutes and dissolved in anhydrous dichloromethane (40 mL). The solution was reduced in volume to 10 mL to induce crystallization. Once crystallization had begun, methylene chloride (20 mL) was added and the cold (0° C.) solution was triturated for 10 minutes. The crystalline product was collected to give 1.72 g (90%) of the hydrochloride (slightly hygroscopic) salt of the starting material.

Method B

Various bis-carbamates (5.00 mmol) were dissolved in 0.010 N HCl in tetrahydrofuran [550 mL, 5.50 mmol HCl; prepared by diluting 1.0 mL concentrated (36.5-38.0%) HCl with 999 mL of anhydrous tetrahydrofuran]. The solution volume was reduced in vacuo to 10 ml with spontaneous cooling to induce crystallization, this mixture was diluted with anhydrous tetrahydrofuran (25 mL) and cooled to 0°-5° C. with stirring for 20 minutes the white crystals that were formed were collected. The formation of the hydrochloride salts of 1-n-propyl-2-(methylthio)-4,5-bis(N-methylcarbonyloxymethyl)imidazole; 1-methyl-2-(n-propylthio)-4,5-bis(N-methylcarbonyloxymethyl) imidazole; and 1-methyl-2-(n-hexylthio)-4,5-bis(N-methylcarbonyloxymethyl)imidazole were produced in quantitative yields from their respective bis-carbamates. 1-n-propyl-2-(methylthio)-4,5-bis(N-methylcarbonyloxymethyl)imidazole hydrochloride salt was produced in 89% yield.

EXAMPLE XVIII

Various bis(acyloxymethyl)imidazole derivatives prepared in accord with Examples I-XVIII and designated Samples A-J, were tested for anti-tumor activity in vivo using the lymphocytic leukemia P-388 test procedure in mice with Samples A and B representing controls. The test system was that employed by the National Cancer Institute (NCI) for the preliminary screening of anti-tumor agents, according to Protocol 1.200 (Cancer Chemo. Reports Part 3, Vol. 3, No. 2, page 9; 1972). In the study ascitic fluid containing $6 \times 10^6$ cells was implanted in the peritoneal cavity of $CDF_1$ female mice. Each imidazole was given in a single injection, at four to six different dose levels (5-6 mice/dose level) daily for five (5) days beginning 24 hours after tumor innoculation. The control animals received saline. Test criteria was in accord with NCI protocol as follows: toxicity day evaluations were carried out on day 5 (number of survivors/number of animals tested); % T/C data was calculated through mean survival time [% T/C=(MST treated/MST control)x100, where MST=mean survival time]; BWD refers to the body weight difference (grams) of test animals compared to control animals; KE refers to the log of the tumor cell population at the end of treatment relative to tumor cell population before treatment.

Table I sets out the identification of the compounds corresponding to the samples used in this and further Examples. Table II sets out the results of the P-388 tests.

EXAMPLE XIX

Tumor cells were inoculated ip(intraperitonal) into female, athymic, mice, being either MX-1 (mammary) or LOX (amelanotic melanoma) human tumor xenograph models. The human xenograft tumors were formed by heterotransplantation of surgically removed human tumors into the subrenal capsule of the nude mice. The nude mice were essentially devoid of T-lymphocytes but appeared to have normal B-lymphocytes and bone marrow progenitors, such that the mice did not reject the xenografts and the human tumors remained viable and progressively preserved with histologic fidelity to the original tumor. The hydrochloride salts of the compounds, designated H, K, and L, and the free base of H, as identified on Table I were administered to the viable human xenograft tumors by a single dose subcutaneous renal cavity (MX-1) injection or interperitonal (LOX) injection to the nude mice test animal in a suspension of 0.9% aqueous sodium chloride solution with "tween-80" and distilled water. The tested compounds were tested against a known cancer tumor inhibiting compound (control) 2,3-dihydro-5-(3'-4'-dichlorophenyl)-6,7-bis(n-propylcarbanoxymethylcarbonate)-1H-pyrollizine.

In both the MX-1 and LOX model, results were expressed as a percentage of the test animal evaluation (T) compared to that for the control (C) and was reported as %T/C. These values are based on all mice in the test.

In the MX-1 model %T/C was evaluated from an estimate of tumor weight in untreated mice as compared to an estimate of tumor weight in treated mice. In such tumor weight evaluation, a low %T/C indicates effective treatment as the tumors of the treated mice are smaller than tumors of the untreated control mice.

In the LOX model %T/C was evaluated by survival, meaning that the mean survival time of mice of the control group surviving (C) is compared to the mean survival time of mice who survived the test with treatment (T). In such survival evaluation, a high %T/C indicates that the treatment is effective.

Table III provides selective results of testing various compounds as above indicated. The data presented comprises findings at optimal dosages of particularly effective compounds of the invention as compared to the control.

TABLE I

| Sample | Compound |
|---|---|
| A | 1-phenyl-4,5-bis(N-methylcarbonyloxymethyl)imidazole |
| B | 1-phenyl-4,5-bis[N-(2-propyl)carbonyloxymethyl]-imidazole |
| C | 1-phenyl-2-methylthio-4,5-bis-(N-methylcarbonyloxymethyl)imidazole |
| D | 1-phenyl-2-methylthio-4,5-bis-[N-(2-propyl)carbonyloxymethyl]imidazole |
| E | 1-benzyl-2-methylthio-4,5-bis-(N-methylcarbonyloxymethyl)imidazole |
| F | 1-benzyl-2-methylthio-4,5-bis-[N-(2-propyl)carbonyloxymethyl)imidazole |
| G | 1-methyl-2-phenyl-4,5-bis-(N-methylcarbonyloxymethyl)imidazole |
| H | 1-methyl-2-methylthio-4,5-bis-(N-methylcarbonyloxymethyl)imidazole |
| I | 1-methyl-2-methylthio-4,5-bis-[N-(2-propyl)carbonyloxymethyl)imidazole |
| J | 1-methyl-2-methoxy-4,5-bis-[N-(2-propyl)carbonyloxymethyl)imidazole |
| K | 1-n-propyl-2-methylthio-4,5-bis-(N-methylcarbonyloxymethyl)imidazole |
| L | 1-n-hexyl-2-methylthio-4,5-bis-(N-methylcarbonyloxymethyl)imidazole |

TABLE II

P-388 Lymphocytic Leukemia Activity

| Sample | Dose/Inj. (mg/kg) | Tox.Day Surv. | BWD (g) | % T/C | KE |
|---|---|---|---|---|---|
| A | 200 | 5/5 | −1.2 | 99 | −1.55 |
| | 100 | 5/5 | −0.4 | 101 | −1.52 |
| | 50 | 5/5 | −0.8 | 101 | −1.52 |
| | 25 | 5/5 | 0.2 | 95 | −1.61 |
| | 12.5 | 5/5 | −0.4 | 99 | −1.55 |
| B | 400 | 6/6 | −2.3 | 90 | toxic |
| | 200 | 6/6 | 0.2 | 90 | toxic |
| | 100 | 6/6 | 0.6 | 91 | −1.69 |
| | 50 | 6/6 | 0.8 | 97 | −1.62 |
| | 25 | 6/6 | −0.1 | 103 | −1.53 |
| | 12.5 | 6/6 | −0.4 | 103 | −1.53 |
| C | 400 | 4/5 | −5.2 | | toxic |
| | 200 | 5/5 | −3.0 | 156 | 1.46 |
| | 100 | 5/5 | −1.6 | 133 | 0.17 |
| | 50 | 5/5 | −1.4 | 141 | 0.60 |
| D | 400 | 6/6 | −4.8 | 100 | −1.52 |
| | 200 | 5/6 | −2.8 | 90 | −1.64 |
| | 100 | 6/6 | −2.0 | 97 | −1.62 |
| | 50 | 6/6 | 0.3 | 95 | −1.64 |
| | 25 | 6/6 | 0.6 | 101 | −1.55 |
| | 12.5 | 6/6 | −0.2 | 111 | −1.42 |
| E | 400 | 6/6 | −1.2 | 127 | −0.71 |
| | 200 | 6/6 | −0.4 | 129 | −0.44 |
| | 100 | 6/6 | 0.4 | 116 | −1.19 |
| | 50 | 6/6 | 0.9 | 116 | −1.19 |
| F | 400 | 3/6 | −3.2 | | toxic |
| | 200 | 6/6 | −2.2 | 116 | −0.32 |
| | 100 | 6/6 | −0.3 | 111 | −0.39 |
| | 50 | 6/6 | −0.5 | 110 | −0.42 |
| | 25 | 6/6 | −1.5 | 101 | −1.59 |
| | 12.5 | 6/6 | −0.2 | 98 | −1.64 |
| G | 200 | 5/5 | −2.2 | 119 | −1.28 |
| | 100 | 5/5 | −1.0 | 116 | −1.31 |
| | 50 | 5/5 | −0.8 | 112 | −1.38 |
| | 25 | 5/5 | 0.0 | 107 | −1.44 |
| | 12.5 | 5/5 | −0.2 | 98 | −1.56 |
| H | 100 | 6/6 | −4.1 | 236 | 6.75 |
| | 50 | 6/6 | −2.6 | 184 | 4.21 |
| | 25 | 6/6 | −1.4 | 147 | 1.05 |
| | 12.5 | 6/6 | −1.2 | 147 | 1.05 |
| | 6.25 | 5/6 | −0.7 | 125 | −0.83 |
| I | 400 | 6/6 | −3.4 | 70 | toxic |
| | 200 | 6/6 | −1.8 | 184 | 4.21 |
| | 100 | 6/6 | −1.2 | 163 | 1.89 |
| | 50 | 6/6 | 0.0 | 130 | −0.56 |
| | 25 | 6/6 | 0.4 | 125 | −0.91 |

TABLE II-continued

P-388 Lymphocytic Leukemia Activity

| Sample | Dose/Inj. (mg/kg) | Tox.Day Surv. | BWD (g) | % T/C | KE |
|---|---|---|---|---|---|
| | 12.5 | 6/6 | 2.6 | 113 | −1.40 |
| J | 400 | 6/6 | −4.2 | 196 | 3.88 |
| | 200 | 6/6 | −2.6 | 189 | 3.41 |
| | 100 | 6/6 | −2.1 | 166 | 1.87 |
| | 50 | 6/6 | −1.0 | 147 | 0.54 |
| | 25 | 6/6 | −0.1 | 130 | −0.60 |

TABLE III

| | MX-1 | | | LOX | | |
|---|---|---|---|---|---|---|
| Sample | Optimal Dosage mg/kg | % T/C wt. | Cures | Optimal Dosage mg/kg | % T/C Survl. | Cures |
| Control | 120 | −92 | — | — | — | — |
| | 120 | −81 | — | — | — | — |
| H (Free base) | 100 | −73 | — | 100 | 365 | 5/6 |
| | 200 | −56 | 2/6 | 100 | 233 | 2/6 |
| H | 115 | −63 | | 115 | 234 | 2/6 |
| K | 240 | Complete Recovery | 6/6 | 240 | 191 | 1/6 |
| L | 270 | Complete Recovery | 6/6 | 135 | 208 | 1/6 |

I claim:

1. A compound of the formula:

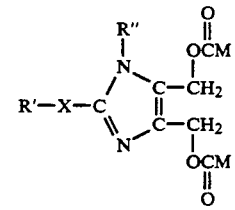

wherein M is

or R; each R, R', and R" are independently selected from hydrogen and Z substituted or unsubstituted hydrocarbon containing from 1-12 carbon atoms and selected from alkyl, cycloalkyl, cycloalkenyl, alkenyl, aryl, and heterocyclic ring wherein each hetero atom is selected from oxygen, nitrogen, sulfur or silicon; provided that $$N\genfrac{}{}{0pt}{}{R}{R}$$

further comprises a Z substituted or unsubstituted heterocyclic ring of 1-12 carbon atoms, and R' and R", combined through the imidazole ring, further comprises a Z substituted or unsubstituted heterocyclic ring of 1-12 carbon atoms wherein said aryl is selected from the aromatic residue of benzene, naphthalene, pyridine, pyrimidine, quinoline, thiophene, indole, phenanthrene, and anthracene and said heterocyclic ring is selected from the group consisting of piperidinyl, pyrrolyl, pyrrolizinyl, pyridyl, imidazolyl, furyl, morpholinyl, piperazyl, thiazolyl, thiomorpholinyl, tetrahydoquinolinyl, oxazolyl, azepinyl, indoxyl, and indolizinyl; wherein S is selected from at least one of oxygen, sulfur, nitrogen and alkylenyl of 1-12 carbon atoms, provided further that silicon is not directly attached to oxygen, sulfur or nitrogen and R' is not hydrogen when X is oxygen or sulfur; and, Z is selected from hydrogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, sulfonylurea, sulfoxide, sulfone, Z substituted and unsubstituted amine or mixtures thereof, provided each Z contains no more than 12 carbon atoms.

2. A compound of the formula:

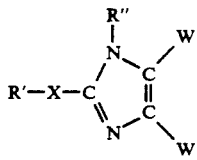

wherein each W is selected from

R'''' is selected from Z substituted and unsubstituted hydrocarbon containing from 1-12 carbon atoms and selected from alkyl, cycloalkyl, cycloalkenyl, alkenyl, and aryl; each R' and R" are independently selected from hydrogen and Z substituted or unsubstituted hydrocarbon containing from 1-12 carbon atoms and selected from alkyl, cycloalkyl, cycloalkenyl, alkenyl, aryl, and heterocyclic ring wherein each hetero atom is selected from oxygen, nitrogen, sulfur or silicon; provided that R' and R", combined through the imidazole ring, further comprises a Z substituted or unsubstituted heterocyclic ring containing up to 12 carbon atoms wherein said aryl is selected from the aromatic residue of benzene, naphthalene, pyridine, pyrimidine, quinoline, thiophene, indole, phenanthrene, and anthracene and said heterocyclic ring is selected from the group consisting of piperidinyl, pyrrolyl, pyrrolizinyl, pyridyl, imidazolyl, furyl, morpholinyl, piperazyl, thiazolyl, thiomorpholinyl, tetrahydoquinolinyl, oxazolyl, azepinyl, indoxyl, and indolizinyl; wherein X is selected from at least one of oxygen, sulfur, nitrogen and alkylenyl of 1-12 carbon atoms; provided further that silicon is not directly attached to oxygen, sulfur or nitrogen and R' is not hydrogen when X is oxygen or sulfur; and, Z is selected from halogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, sulfonylurea, sulfoxide, sulfone, amine or mixtures thereof, provided that each Z contains no more than about 12 carbon atoms.

3. A compound of the formula:

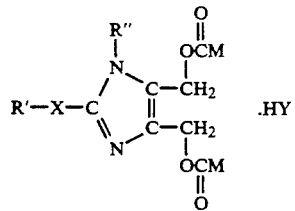

wherein Y is the anion of an acid; M is

or R; each R, R', and R" are independently selected from hydrogen and Z substituted or unsubstituted hydrocarbon of 1-12 carbon atoms selected from alkyl, cycloalkyl, cycloalkenyl, alkenyl, aryl, and heterocyclic ring wherein each hetero atom is selected from oxygen, nitrogen, sulfur or silicon; provided that N<RR further comprises a Z substituted or unsubstituted heterocyclic ring containing up to 12 carbon atoms, and R' and R", combined through the imidazole ring, further comprises a Z substituted or unsubstituted heterocyclic ring containing up to 12 carbon atoms wherein said aryl is selected from the aromatic residue of benzene, naphthalene, pyridine, pyrimidine, quinoline, thiophene, indole, phenanthrene, and anthracene and said heterocyclic ring is selected from the group consisting of piperidinyl, pyrrolyl, pyrrolizinyl, pyridyl, imidazolyl, furyl, morpholinyl, piperazyl, thiazolyl, thiomorpholinyl, tetrahydroquinolinyl, oxazolyl, azepinyl, indoxyl, and indolizinyl; wherein X is selected from at least one of oxygen, sulfur, nitrogen and alkylenyl of 1-12 carbon atoms; provided further that silicon is not directly attached to oxygen, sulfur or nitrogen and R' is not hydrogen when X is oxygen or sulfur; and, Z is selected from halogen, nitro, nitrile, alkyl, haloalkyl, alkenyl, carboxylic acid, carboxylic acid ester, carboxylic acid amide, ether, thioether, hydroxyl, acylated hydroxyl, sulfonylamide, sulfonylurea, sulfoxide, sulfone, amine or mixtures thereof, provided each Z contains no more than about 12 carbon atoms.

4. A compound of claim 1 wherein M is selected from hydrogen and Z substituted or unsubstituted alkyl, cycloalkyl, cycloalkenyl, alkenyl, and aryl.

5. A compound of claim 1 wherein M is selected from N<RR and R is selected from hydrogen and Z substituted and unsubstituted alkyl, cycloalkyl, cycloalkenyl, alkenyl, and aryl.

6. A compound of claim 1 wherein X is oxygen.

7. A compound of claim 1 wherein X is sulfur.

8. A compound of claim 1 wherein X is nitrogen.

9. A compound of claim 1 wherein X is alkyl.

10. A compound of claim 1 wherein R' and R" are selected from hydrogen and Z substituted or unsubstituted alkyl, cycloalkyl, cycloalkenyl, alkenyl, and aryl.

11. A compound of claim 10 wherein X is sulfur.

12. A compound of claim 5 wherein X is sulfur and R' and R" are selected from hydrogen and Z substituted or unsubstituted alkyl, cycloalkyl, cycloalkenyl, alkenyl, and aryl.

13. A compound of claim 12 wherein R, R', and R" are selected from hydrogen, alkyl, cycloalkyl, and aryl.

14. A compound of claim 13 selected from 1-phenyl-2-methylthio-4,5-bis(N-methylcarbonyloxymethyl)imidazole; 1-phenyl-2-methylthio-4,5-bis [N-(2-propyl)carbonyloxymethyl]imidazole; 1-benzyl-2-methylthio-4,5-bis (N-methylcarbonyloxymethyl)imidazole; 1-benzyl-2-methylthio-4,5-bis [N-(2-propyl)carbonyloxymethyl)imidazole; 1-methyl-2-phenyl-4,5-bis(N-methylcarbonyloxymethyl)imidazole; 1-methyl-2-methylthio-4,5-bis(N-methylcarbonyloxymethyl)imidazole; 1-methyl-2-methylthio-4,5-bis[N-(2-propyl)-carbonyloxymethyl) imidazole; 1-methyl-2-methoxy-4,5-bis[N-(2-propyl)carbonyloxymethyl)imidazole; 1-n-propyl-2-methylthio-4,5-bis(N-methylcarbonyloxymethyl)imidazole; and 1-n-hexyl-2-methylthio-4,5-bis (N-methylcarbonyloxymethyl) imidazole.

15. The 1-methyl-2-methylthio-4,5-bis(N-methylcarbonyloxymethyl) imidazole compound of claim 14.

16. The 1-n-propyl-2-methylthio-4,5-bis(N-methylcarbonyloxymethyl) imidazole compound of claim 14.

17. The 1-n-hexyl-2-methylthio-4,5-bis (N-methylcarbonyloxymethyl) imidazole compound of claim 14.

18. A compound of claim 2 wherein W is -C OR'''.

19. A compound of claim 18 wherein R' and R'' are selected from hydrogen, alkyl, cycloalkyl, cycloalkenyl, alkenyl, and aryl.

20. A compound of claim 19 wherein X is selected from oxygen and sulfur.

21. A compound of claim 3 wherein M is selected from hydrogen and Z substituted or unsubstituted alkyl, cycloalkyl, cycloalkenyl, alkenyl, and aryl.

22. A compound of claim 3 wherein M is selected from N<RR and R is selected from hydrogen and Z substituted and unsubstituted alkyl, cycloalkyl, cycloalkenyl, alkenyl, and aryl.

23. A compound of claim 3 wherein X is oxygen.

24. A compound of claim 3 wherein X is sulfur.

25. A compound of claim 3 wherein X is nitrogen.

26. A compound of claim 3 wherein X is alkyl.

27. A compound of claim 3 wherein R' and R'' are selected from hydrogen and Z substituted or unsubstituted alkyl, cycloalkyl, cycloalkenyl, alkenyl, and aryl.

28. A compound of claim 27 wherein X is sulfur.

29. A compound of claim 22 wherein X is sulfur and R' and R'' are selected from hydrogen and Z substituted or unsubstituted alkyl, cycloalkyl, cycloalkenyl, alkenyl, and aryl.

30. A compound of claim 29 wherein R, R', and R'' are selected from hydrogen, alkyl, cycloalkyl, and aryl.

31. A compound of claim 30 selected from an acid salt of 1-phenyl-2-methylthio-4,5-bis (N-methylcarbonyloxymethyl)imidazole; 1-phenyl-2-methyl-thio-4,5-bis[N-(2-propyl)carbonyloxymethyl]imidazole; 1-benzyl-2-methylthio-4,5-bis(N-methylcarbonyloxymethyl)imidazole; 1 -benzyl-2-methylthio-4,5-bis[N-(2-propyl)carbonyloxymethyl)imidazole; 1-methyl-2-phenyl-4,5-bis(N-methylcarbonyloxymethyl)imidazole; 1 -methyl-2-methylthio-4,5-bis(N-methylcarbonyloxymethyl)imidazole; 1 -methyl-2-methylthio-4,5-bis [N-(2-propyl)carbonyloxymethyl)imidazole; 1-methyl-2-methoxy-4,5-bis [N-(2-propyl)carbonyloxymethyl)imidazole; 1-n-propyl-2-methylthio-4,5-bis (N-methylcarbonyloxymethyl)imidazole; and 1-n-hexyl-2-methylthio-4,5-bis (N-methylcarbonyloxymethyl)imidazole.

32. The 1-methyl-2-methylthio-4,5-bis(N-methylcarbonyloxymethyl) imidazole acid salt compound of claim 30.

33. The 1-n-propyl-2-methylthio-4,5-bis (N-methylcarbonyloxymethyl)imidazole acid salt compound of claim 30.

34. The 1-n-hexyl-2-methylthio-4,5-bis (N-methylcarbonyloxymethyl) imidazole acid salt compound of claim 30.

35. The hydrochloric acid salt of a compound of claim 31.

36. A composition comprising a microorganism inhibiting effective toxic amount of a compound of claim 1 and a diluent.

37. A composition of claim 36 wherein the compound is selected from 1-phenyl-2-methylthio-4,5-bis(N-methyl-carbonyloxy-methyl)imidazole; 1-phenyl-2-methyl-thio-4,5-bis[N-(2-propyl) carbonyloxymethyl]imidazole; 1-benzyl-2-methylthio-4,5-bis(N-methylcarbonyloxymethyl)imidazole; 1-benzyl-2-methylthio-4,5-bis[N-(2-propyl)carbonyloxymethyl)imidazole; 1-methyl-2-phenyl-4,5-bis(N-methylcarbonyloxymethyl)imidazole; 1-methyl-2-methylthio-4,5-bis(N-methylcarbonyloxymethyl)imidazole; 1-methyl-2-methylthio-4,5-bis(N-(2-propyl)carbonyloxymethyl) imidazole; 1-methyl-2-methoxy-4,5bis[N-(2-propyl)carbonyloxymethyl)imidazole; 1-n-propyl-2-methylthio-4,5-bis(N-methyl-carbonyloxy-methyl) imidazole; and 1-n-hexyl-2-methylthio-4,5-bis(N-methyl-carbonyloxymethyl)imidazole.

38. A composition of claim 37 wherein the compound is 1-methyl-2-methylthio-4,5-bis(N-methylcarbonyloxymethyl) imidazole.

39. A composition of claim 39 wherein the compound is 1-n-propyl-2-methylthio-4,5-bis(N-methylcarbonyloxy-methyl)imidazole.

40. A composition of claim 37 wherein the compound is 1n-hexyl-2-methylthio-4,5-bis(N-methylcarbonyloxymethyl) imidazole.

41. A composition comprising the microorganism inhibiting effective toxic amount of a compound of claim 3 and a diluent.

42. A composition of claim 41 wherein the compound is selected from an acid salt of 1-phenyl-2-methylthio-4,5-bis(N-methyl-carbonyloxymethyl)imidazole; 1-phenyl-2-methyl-thio-4,5-bis[N-(2-propyl)carbonyloxymethyl]imidazole; 1-benzyl-2-methyl-thio-4,5-bis(N-methylcarbonyloxymethyl)imidazole; 1-benzyl-2-methylthio-4,5-bis[N-(2-propyl)carbonyloxymethyl) imidazole; 1-methyl-2-phenyl-4,5-bis(N-methylcarbonyloxymethyl) imidazole; 1-methyl-2-methylthio-4,5-bis(N-methylcarbonyloxymethyl)imidazole; 1-methyl-2-methylthio-4,5-bis[N-(2-propyl)carbonyloxymethyl) imidazole; 1-methyl-2-methoxy-4,5-bis[N-2-propyl)carbonyloxy-methyl) imidazole; 1-n-propyl-2-methylthio-4,5-bis(N-methylcarbonyloxy-methyl)imidazole; and 1-n-hexyl-2-methylthio-4,5-bis(N-methylcarbonyloxymethyl)imidazole.

43. A composition of claim 42 wherein the compound is a 1-methyl-2-methylthio-4,5-bis(N-methylcarbonyloxymethyl) imidazole acid salt.

44. A composition of claim 42 wherein the compound is a 1-n-propyl-2-methylthio-4,5-bis(N-methylcarbonyloxymethyl) imidazole acid salt.

45. A composition of claim 42 wherein the compound is a 1-n-hexyl-2-methylthio-4,5-bis(N-methylcarbonyloxymethyl) imidazole acid salt.

* * * * *